US008101198B2

(12) United States Patent
Ogawa et al.

(10) Patent No.: US 8,101,198 B2
(45) Date of Patent: Jan. 24, 2012

(54) OSTEOGENIC ENHANCER COMPOSITION

(75) Inventors: Takahiro Ogawa, Torrence, CA (US); Anahid Jewett, Valencia, CA (US)

(73) Assignee: The Regents of the University of California, Oakland, CA (US)

( * ) Notice: Subject to any disclaimer, the term of this patent is extended or adjusted under 35 U.S.C. 154(b) by 101 days.

(21) Appl. No.: 12/374,475

(22) PCT Filed: Jul. 25, 2007

(86) PCT No.: PCT/US2007/016825
§ 371 (c)(1),
(2), (4) Date: Jan. 20, 2009

(87) PCT Pub. No.: WO2008/013900
PCT Pub. Date: Jan. 31, 2008

(65) Prior Publication Data
US 2009/0324669 A1 Dec. 31, 2009

(51) Int. Cl.
A61F 13/00 (2006.01)
A61K 38/17 (2006.01)
A61K 38/18 (2006.01)

(52) U.S. Cl. ........... 424/422; 514/8.9; 514/8.1; 514/9.1; 514/8.5; 514/16.7; 514/17.1; 514/17.2

(58) Field of Classification Search .......................... None
See application file for complete search history.

(56) References Cited

U.S. PATENT DOCUMENTS

| 4,563,489 | A | | 1/1986 | Urist | |
|---|---|---|---|---|---|
| 5,124,151 | A | | 6/1992 | Viegas et al. | |
| 5,208,014 | A | * | 5/1993 | Dubief et al. | 424/70.51 |
| 5,385,887 | A | | 1/1995 | Yim et al. | |
| 5,410,016 | A | | 4/1995 | Hubbell et al. | |
| 5,932,299 | A | | 8/1999 | Katoot | |
| 6,333,304 | B1 | * | 12/2001 | Bath et al. | 514/17.2 |
| 6,702,855 | B1 | | 3/2004 | Steinemann et al. | |
| 7,754,686 | B2 | * | 7/2010 | Hageman et al. | 514/9.1 |
| 2002/0187104 | A1 | | 12/2002 | Li et al. | |
| 2004/0210309 | A1 | | 10/2004 | Denzer et al. | |
| 2004/0247570 | A1 | * | 12/2004 | Miller et al. | 424/93.7 |
| 2008/0299204 | A1 | * | 12/2008 | Nangia et al. | 424/489 |

FOREIGN PATENT DOCUMENTS

| JP | 8257110 | 10/1996 |
|---|---|---|
| WO | WO 95/05846 | 3/1995 |
| WO | WO 97/31661 | 9/1997 |
| WO | WO 97/34016 | 9/1997 |
| WO | WO 00/71083 | 11/2000 |
| WO | WO 02/085422 | 10/2002 |
| WO | WO 03/024316 | 3/2003 |
| WO | WO 2004/005421 | 1/2004 |

OTHER PUBLICATIONS

Rocsen et al., Clin Exp Immunol, 122:249-256, 2000.*
Bhandari et al., "Predictors of In-Hospital Mortality Following Operative Mangement of Hip Fractures", J. of Surg. Investigation vol. 1, No. 4, pp. 319-326 (1999).
Campion et al., "Hip Fracture: A Prospective Study of Hospital Complications, and Costs", J. of Gen. Internal Medicine vol. 2, pp. 78-82 (1987).
Cortizo et al, "A possible role of oxidative stress in the vanadium-induced cytotoxicity in the MC3T3E1 osteoblast and UMR106 osteosarcoma cell lines", Toxicology 147, pp. 89-99 (2000).
Espehaug et al., "The type of cement and failure of total hip replacements", The J. of Bone and Joint Surgery vol. 84-B, No. 6, pp. 832-838 (2002).
Fox Ray et al., "Medical Expenditures for the Treatment of Osteoporotic Fractures in the United States in 1995: Report from the National Osteoporosis Foundation", J. of Bone and Mineral Res. vol. 12, No. 1, pp. 24-35 (1997).
Gillissen et al., "Antioxidant Function of Ambroxol in Mononuclear and Polymorphonuclear Cells in Vitro", Lung 175, pp. 235-242 (1997).
Govender et al., "Recombinant Human Bone Morphogenetic Protein-2 for Treatment of Open Tibial Fractures", J. of Bone & Joint Surgery, pp. 2123-2134 (2002).
Guccione et al., "Regaining Functional Independence in the Acute Care Setting Following Hip Fracture", Phys. Therapy, vol. 76, No. 8, pp. 818-826 (1996).
Guk Park et al., "Role of mitogen-activated protein kinases in hydrogen peroxide-induced cell death in osteoblastic cells", Toxicology 215, pp. 115-125 (2005).
Gutowska et al., "Injectable Gels for Tissue engineering", The Anatomical Record 263, pp. 342-349 (2001).
Hudson et al., "Eight-Year Outcome Associated with Clinical Options in the Mnagement of Femoral Neck Fractures", Clin. Ortho. and Related Research No. 348, pp. 59-66 (1998).
Lamade et al., "Bone cement implantation syndrome, a prospective randomised trial for use of antihistamine blockade", Arch. Orthop. Trauma Surg. 114, pp. 335-339 (1995).
Lean et al., "A crucial role for thiol antioxidants in estrogen-deficiency bone loss", The J. of Clinical Investigation vol. 112, No. 6, pp. 915-923 (2003).
Lu-Yao et al., "Outcomes after Displaced Fractures of the Femoral Neck", The J. of Bone and Joint Surgery vol. 76-A, No. 1, pp. 15-25 (1994).
Mody et al., "Oxidative stress modulates osteoblastic differentiation of vascular and bone cells", Free Radical Biology and Medicine vol. 31, No. 4, pp. 509-519 (2001).

(Continued)

Primary Examiner — Marianne P Allen
(74) Attorney, Agent, or Firm — Squire, Sanders & Dempsey (US) LLP

(57) ABSTRACT

An osteogenic enhancer composition for bone and cartilage repair and methods of using the same are described.

11 Claims, 8 Drawing Sheets

OTHER PUBLICATIONS

Ogawa et al., "Biomechanical Evaluation of Osseous Implants Having Different Surface Topographies in Rats", J. Dent. Res. 79 (11), 1857-1863 (2000).

Ratanasathien et al., "Cytotoxic Interactive Effects of Dentin Bonding Components on Mouse Fibroblasts", J. Dent. Res. 74, (9), pp. 1602-1606 (1995).

Ravikumar et al., "Internal fixation versus hemiarthroplasty versus total hip arthroplasty for displaced subcapital fractures of femur-13 year results of a prospective randomized study", Injury, Int. J. Care Injured 31, pp. 793-797 (2000).

Stanislawski et al., "Dental restorative biomaterials induce glutathione depletion in cultured human gingival fibroblast: Protective effect of N-acetyl cysteine", Introduction of GSH Depletion in Fibroblast, pp. 469-474 (2000).

Takada et al., "Sulfated Polysaccharides Enhance the Biological Activities of Bone Morphogenetic Proteins", The J. of Biol. Chem. vol. 278, No. 44, pp. 43229-43235 (2003).

Tidermark et al., "Internal fixation compared with total hip replacement for displaced femoral neck fractures in the elderly", The J. of Bone and Joint Surgery vol. 85-B, No. 3, pp. 380-388 (2003).

Tidermark et al., "Quality of Life Related to Fracture Displacement Among Elderly Patients with Femoral Neck Fractures Treated with Internal Fixation", J. of Orthopedic Trauma vol. 16, No. 1, pp. 34-38 (2002).

Weinstein et al., "Apoptosis and Osteoporosis", The Am. J. of Medicine vol. 108, pp. 153-164 (2000).

Xiao-chun Bai et al., "Oxidative stress inhibits osteoblastic differentiation of bone cells by ERK and NF-kB", Biochem. and Biophysical Res. Comm. 314, pp. 197-207 (2004).

Jennissen et al., "Biocoating of implants with mediator molecules: surface enhancement of metals by treatment with chromosulfuric acid", Mat. Wiss. u. Werkstofftech 30, pp. 838-845 (1999).

Voggenreiter et al., "Assesment of the biological activity of chemically immobilized rhMNP-2 on titanium surfaces in vivo", Mat. Wiss. u. Werkstofftech 32, pp. 942-948 (2001).

* cited by examiner

OSTEOGENIC ENHANCER COMPOSITION

FIELD OF THE INVENTION

This invention generally relates to an osteogenic enhancer composition and methods of using the same.

DESCRIPTION OF THE BACKGROUND

Osteoporotic femoral neck fracture and degenerative changes of knee and hip joints are common problems. For example, there are over 300,000 incidence of hip fracture reconstruction alone in the U.S., with a considerable degree of post-treatment disability (Campion E W, et al., *J Gen Intern Med* 2:78-82 (1987)), long-lasting independence (Guccione A. A, et al., *Phys Ther* 76:818-26 (1996)), post-surgical mortality causing from the use of bone cement (Bhandari M, et al., *Int J Surg Investig* 1:319-26 (1999)), high percentage of the revision surgery ranging 5%-40% (Espehaug B, et al., *J Bone Joint Surg Br* 84:832-8 (2002); Hudson J I, et al., *Clin Orthop Relat Res:* 59-66 (1998); Lu-Yao G L, et al., *J Bone Joint Surg Am* 76:15-25 (1994); Ravikumar and Marsh *Injury* 31:793-7 (2000); Tidermark J, et al., *J Bone Joint Surg Br* 85:380-8 (2003) and substantial reduction of quality of life (Tidermark J, et al., *J Bone Joint Surg Br* 85:380-8 (2003); Tidermark J, et al., *J Orthop Trauma* 17:S17-21 (2002)) Annual expenditures for the treatment of osteoporotic fractures are estimated at $13.8 billion (Ray N F, Chan J K, Thamer M, Melton L J, 3rd (1997). Medical expenditures for the treatment of osteoporotic fractures in the United States in 1995: report from the National Osteoporosis Foundation. *J Bone Miner Res* 12:24-35). The use of metallic implants as an anchor has become an essential measure for reconstructive treatment of such cases.

Bone regenerative therapy using growth factors has some success. For example, recombinant bone morphogenetic proteins (BMPs), as represented by BMP2 and BMP7, are the emerging therapeutic agents for bone regenerative therapy. In vitro, BMPs stimulate the differentiation of multopotential mesenchymal stem cells into osteoblastic linage. Osteoinductive capability of BMPS was demonstrated in ectopic sites in vivo. BMPs have key roles in development, growth and repair of bone. Limited FDA approval was recently obtained for the use of BMPs in selected applications, such as spine fusions and non-unions. Clinically, BMPs seem to be effective only when used in high dose (Govender S, et al., *J Bone Joint Surg Am* 84-A: 2123-2134 (2002)). However, although the proved overall effects of BMPs on promoting fracture healing and reducing infection rate, inconsistency is found in its effectiveness: the significant percentage of patients are not suseptable for the BMPs (Govender et al., 2002, supra). Inherently, BMPs involves concerns in protein degradation, mode of delivery and high cost.

Severe adverse effects of bone cement on systemic conditions have been reported. Bone cement implantation syndrome (BCIS) is characterized by hypotension, hypoxaemia, cardiac arrhythmias, cardiac arrest or any combination of these, leading to an immediate death in 0.6-1% of the recipients ((Bhandari M, et al., *Int J Surg Investig* 1:319-26 (1999); Lamade W R, et al., *Arch Orthop Trauma Surg* 114:335-9 (1995)).

Therefore, there is a need for osteogenic enhancer composition for bone and/or cartilage repair.

The composition and methods of making the polymer and implantable materials disclosed herein address the above described problems.

SUMMARY OF THE INVENTION

Provided herein is an osteogenic enhancer composition. The composition can include an effective amount of an osteogenic enhancing molecule. In some embodiments, the osteogenic enhancing molecule is N-acetyl cysteine (NAC). The composition is effective for the bone regenerative and reconstructive therapy and bone engineering.

As used herein, the term "effective amount" refers to an amount of the osteogenic enhancer molecule effective for promoting oesteoblastic differentiation in a mammal, e.g., a human being. In some embodiments, the effective amount can range from about 1 ng/L to about 100 g/L. In some embodiments, the effective amount can range from about 0.1 ng/ml to 500 µg/ml, from about 0.1 µg/ml to about 1.5 µg/ml, or from about 0.1 µg/ml to about 4 µg/ml.

The composition can be formulated into any desirable formulation for bone and cartilage regeneration/repair and healing.

The composition described herein can have a variety of applications. In some embodiments, the composition can be formulated into bone cement. In some embodiments, the composition can be a scaffold for cartilage, bone or vertebral tissue engineering and repair. The composition can be used to treat, prevent or ameliorate a bone, cartilage or vertebra related condition.

7B) of the rat osteoblastic cells cultured on bone cement materials with or without NAC-incorporation. Data are shown as the mean±SD (n=3).

Figure 8:
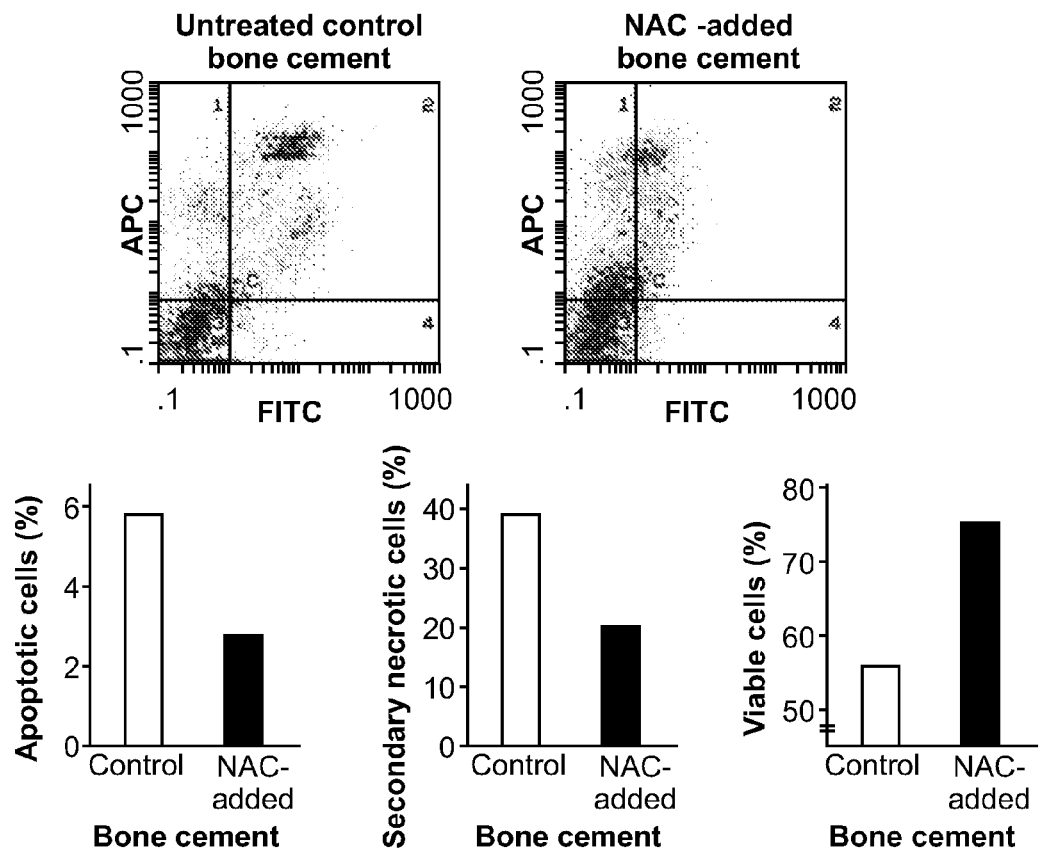

FIG. 8 shows the results from cell apoptosis analysis performed for the rat bone marrow-derived osteoblastic cells cultured on the untreated control bone cement and NAC-added bone cement for 24 hours. The flowcytometric images are shown on the top, and the percentages of apoptotic cells (area 4 on the top images), secondary necrotic cells (area 2) and viable cells (areas 1 and 3) are shown in the bottom.

Figure 9:
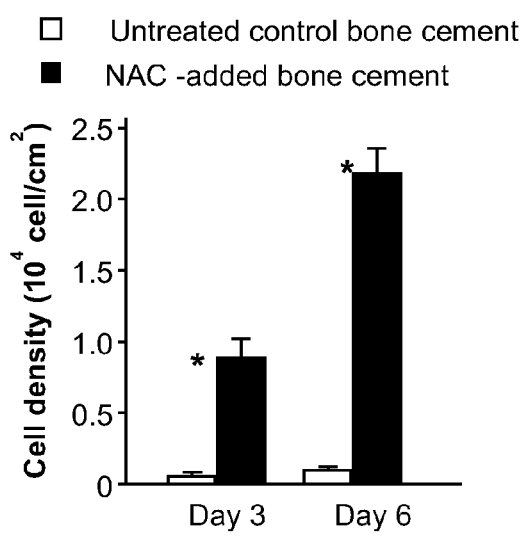

FIG. 9 shows osteoblastic cell proliferative activity measured by cell density at days 3 and 6 of culture. The rat bone marrow-derived osteoblastic cells were cultured on bone cement with or without NAC addition. Data are shown as the mean±SD (n=3) (the symbol "*" indicates that the data is statistically significant between the control and NAC-added bone cement samples, p<0.0001).

Figure 10A:
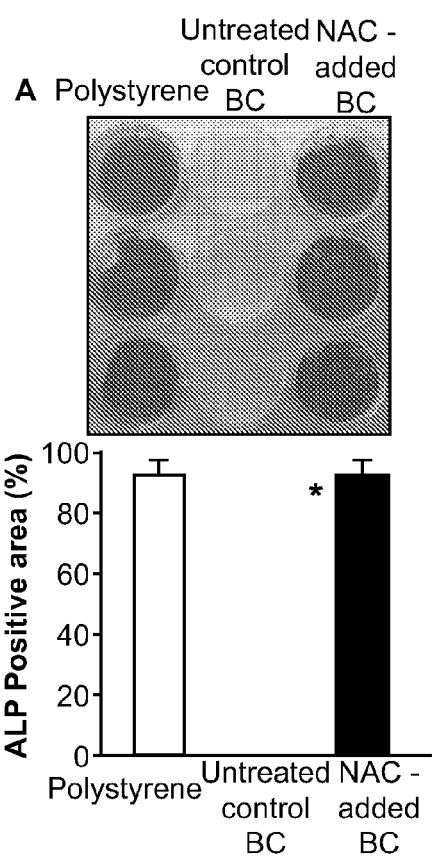
Figure 10B:
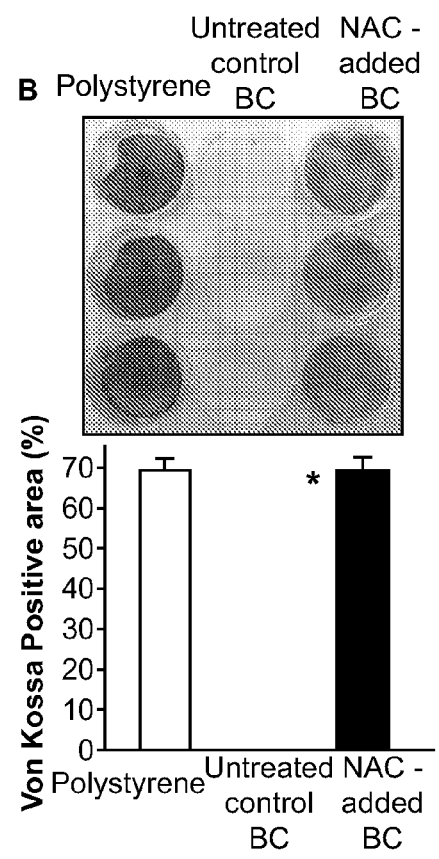

FIG. 10A shows alkaline phosphatase activity of osteoblasts restored by NAC. FIG. 10B shows mineralizing capability of osteoblasts on NAC-added bone cement.

Figure 11A:
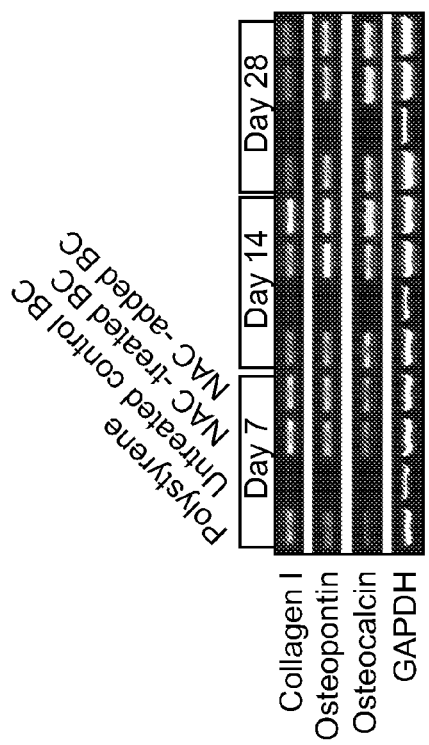
Figure 11B:
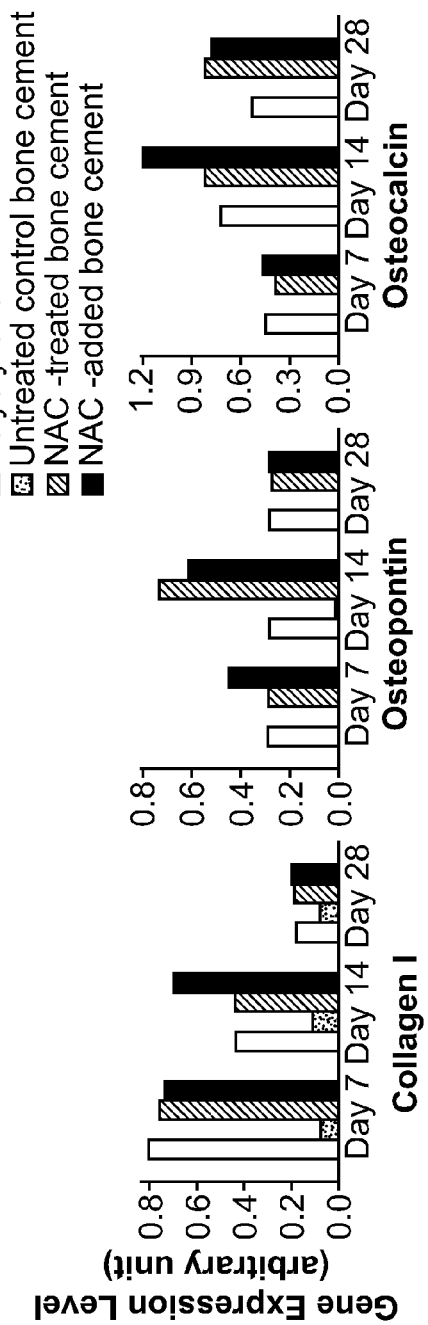

FIGS. 11A and 11B show gene expression analysis in the osteoblastic cultures on the polystyrene, control bone cement, bone cement with NAC in the media or NAC-added bone cement. FIG. 11A shows a result of electrophoresis after RT-PCR. FIG. 11B shows quantitative gene expression levels of collagen I, osteopontin and osteocalcin genes relative to the GAPDH expression.

FIGS. 12A-12D show biomechanical properties of control bone cement and NAC-added bone cement. Data are shown as the mean±SD (n=5).

DETAILED DESCRIPTION

Provided herein is an osteogenic enhancer composition. The composition can include an effective amount of an osteogenic enhancing molecule. In some embodiments, the osteogenic enhancing molecule is N-acetyl cysteine (NAC). The composition is effective for the bone regenerative and reconstructive therapy and bone engineering. For example, the composition is effective for wound healing, repair, generation or regeneration of a bone or cartilage tissue.

As used herein, the term "effective amount" refers to an amount of the osteogenic enhancer molecule effective for promoting oesteoblastic differentiation in a mammal, e.g., a human being. In some embodiments, the effective amount can range from about 1 ng/L to about 100 g/L. In some embodiments, the effective amount can range from about 0.1 ng/ml to 500 µg/ml, from about 0.1 µg/ml to about 1.5 µg/ml, or from about 0.1 µg/ml to about 4 µg/ml.

The term "enhancing" refers to an enhancing effect of at least about 1%, about 5%, about 10%, about 20%, about 30%, about 40%, about 50%, about 60%, about 70%, about 80%, about 90%, or about 100% or above enhancement of a biological process or mechanism, e.g., an osteogenic process or mechanism.

The composition can be formulated into any desirable formulation for bone and cartilage regeneration/repair.

Oxidative Stress

Osteoblasts are constantly exposed to various types of oxidative stress. For instance, free radical oxidants, such as super oxide anion, hydrogen peroxide and hydroxyl radicals, are generated as inflammatory or responsive molecules during the fracture healing process, as well as during the normal cellular metabolism.

Oxidative stress is known to induce cell apoptosis in a wide variety of cell types, including osteoblasts (Cortizo A M, et al., *Toxicology* 147: 89-99 (2000)), by modulating intracellular signaling pathway, extracellular signal-regulated kinase (ERK) activation (Park B G, et al., *Toxicology* 215: 115-125 (2005)). Recent studies showed that oxidative stress inhibits osteoblastic differentiation (Mody N, et al. *Free Radic Biol Med* 31: 509-519 (2001)), through ERK and ERK-dependent NF-kappaB activation (Bai X C, et al., *Biochem Biophys Res Commun* 314: 197-207 (2004)).

Oxidant-induced apoptosis of osteoblastic cells may be associated with the pathogenesis of bone metabolic diseases, such as osteoporosis (Weinstein R S, Manolagas S C, *Am J Med* 108: 153-164 (2000)). Glutathione is a cysteine derivative primarily located in the cell membrane, and glutathione-mediated redox cycle is the most important removal system for free radicals (see, e.g., Stanislawski L, et al., *J Biomed Mater Res* 51:469-74 (2003)).

Osteogenic Enhancer Molecule

The osteogenic enhancer molecule can be any osteogenic enhancer molecule that is effective for promoting oesteoblastic differentiation in a mammal, e.g., a human being.

In some embodiments, the osteogenic enhancer molecule can include an antioxidant. The antioxidant can include, but is not limited to, antioxidative amino-acids such as N-acetyl cysteine (NAC), cysteine, cysteine derivatives, glutathione, or glutathione derivatives, glutathione peroxidase, vitamins such as vitamin C (ascorbic acid) and vitamin E, beta carotene, flavonoids, ubiquinone, butylated hydroxytoluene (BHT), butylated hydroxyanisole (BHA), superoxide dismutase (SOD) or superoxide dismutase mimetic (which is also commonly referred to as superoxide dismutase mimic) (SODm) or combinations thereof.

NAC is an anti-oxidant cysteine derivative produced by the most types of cells. NAC can be easily deacetylated into cysteine, which is an important precursor of glutathione (see, e.g., Lean J M, et al., *J Clin Invest* 112:915-23 (2003)), and helps promote the cellular glutathione system (see, e.g., Gillissen A, et al., *Lung* 175:235-42 (1997)). NAC also directly acts as an strong oxidant scavenger (Gillissen et al., 1997). Therefore, NAC can reduce oxidative stress.

In some embodiments, the antioxidant can be an extract of a plant or animal or a compound isolated therefrom capable of reducing oxidative stress. For example, the extract can be an extract of green tea, pine bark, grape skin, grape seed, or combinations thereof.

The inclusion of an antioxidant, such as NAC, to bone cement was demonstrated not to compromise the mechanical properties of the bone cement. In some embodiments, the bone cement described herein can exclude any of the specifically listed antioxidants.

The composition described herein can have a variety of applications. In some embodiments, the composition can be formulated into bone cement. In some embodiments, the composition can be a scaffold for cartilage, bone or vertebral tissue engineering and repair. The composition can be used to treat, prevent or ameliorate a bone, cartilage or vertebra related condition.

Bioactive Agents

In some embodiments, the formulation can include a bioactive agent. The bioactive agent can be any bioactive agent. In some embodiments, the bioactive agent can be an adhesion molecule, a bone growth factor, a transforming growth factor (TGF), a transcription factor, fibroblast growth factor (FGF), an insulin like growth factor (IGF), a vascular endothelial growth factor (VEGF), a hormone, an anti-inflammatory agent, calcium phosphate, vitamin, an osteogenic cell, an osteoblastic cell, or combinations thereof. In some embodiments, the bioactive agent can be collagen, a bone matrix, a tendon matrix or ligament matrix, or combinations thereof.

Some examples of the adhesive molecule can be, but are not limited to, an RGD or cyclic RGD peptide (or mimetics of RGD or mimetic of cyclic RGD peptide), or a vascular cell adhesion Molecule (VCAM).

Some examples of the growth factor can be, but are not limited to, bone morphological proteins (BMP) such as BMP2, BMP4, or BMP7.

Some examples of the transcription factors can be, but are not limited to, Runx2/cbfa1.

Some examples of fibroblast growth factors (FGFs) are alpha-FGF or beta-FGF.

Some examples of calcium phosphate can be hydroxyapatite and tri-calcium phosphate.

Some examples of vitamins can be vitamin D.

Some examples of the anti-inflammatory agent include, but are not limited to, steroidal or non-steroidal anti-inflammatory agents, glucocorticoids such as dexamethasone, betamethasone, and cortisone.

In some embodiments, the composition can explicitly exclude any of the bioactive agents mentioned above.

Formulation

The composition described herein can be formulated into any desirable formulation. In some embodiments, the formulation can be a cement for bone, cartilage, or vertebra. In some embodiments, the formulation can be a scaffold for bone, cartilage, or vertebra.

In some embodiments, the composition can be a bone graft substitute, collagen gel, collagen membrane, collagen sponge and bone cement with enhanced osteoconductive capacity. In some embodiments, the composition can be a coating applied onto metallic and nonmetallic endosseous implants.

In some embodiments, for example, the formulation can be bone cement. In some embodiments, the formulation can be a scaffold for cartilage or vertebral repair.

In some embodiments, the composition can comprise a wound healing material for bone or cartilage.

In some embodiments, the composition can be in a formulation for jaw and craniofacial areas for wound healing, repair, generation and regeneration.

The formulation can include any material currently in use in the art. In one embodiment, the formulation can optionally include a biologically or pharmaceutically compatible carrier. In some embodiments, the carrier can be a polymeric carrier that is a synthetic or natural polymer, which can be biodegradable, such as degradable by enzymatic or hydrolytic mechanisms. Examples of polymeric carriers include, but are not limited to synthetic absorbable polymers such as such as but not limited to poly($\alpha$-hydroxy acids) such as poly(L-lactide) (PLLA), poly(D, L-lactide) (PDLLA), polyglycolide (PGA), poly(lactide-co-glycolide) (PLGA), poly(caprolactone), poly(trimethylene carbonate), poly(p-dioxanone), poly(caprolactone-co-glycolide), poly(glycolide-co-trimethylene carbonate) poly(D, L-lactide-co-trimethylene carbonate), polyarylates, polyhydroxybutyrate (PHB), polyanhydrides, poly(anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly(glax-anone), polysaccharides, and poly(orthoesters), polyglactin, polyglactic acid, polyaldonic acid, polyacrylic acids, polyalkanoates, copolymers and admixtures thereof, and any derivatives and modifications (See for example, U.S. Pat. No. 4,563,489, and PCT Int. Appl. # WO/03024316, herein incorporated by reference). Other examples of carriers include cellulosic polymers such as, but not limited to alkylcellulose, hydroxyalkylcellulose, methylcellulose, ethylcellulose, hydroxyethylcellulose, hydroxypropylcellulose, hydroxypropyl-methylcellulose, carboxymethylcellulose, and their cationic salts. Other examples of carriers include synthetic and natural bioceramics such as, but not limited to calcium carbonates, calcium phosphates, apatites, bioactive glass materials, and coral-derived apatites. See for example U.S. Patent Application 2002187104; PCT Int. Appl. WO/9731661; and PCT Int. Appl. WO/0071083, herein incorporated by reference.

Other examples of carriers include collagen (e.g. Collastat, Helistat collagen sponges), hyaluronan, fibrin, chitosan, alginate, and gelatin, or a mixture thereof. See for example, PCT Int. Appls. WO/9505846; WO/02085422, the teachings of which are incorporated herein by reference.

In one embodiment, the carrier may include heparin-binding agents; including but not limited to heparin-like polymers e.g. dextran sulfate, chondroitin sulfate, heparin sulfate, fucan, alginate, or their derivatives; and peptide fragments with amino acid modifications to increase heparin affinity. See for example, Journal of Biological Chemistry (2003), 278 (44), p. 43229-43235, the teachings of which are incorporated herein by reference.

In one embodiment, the formulation can be in the form of a flowable gel. The gel may be selected so as to be injectable, such as via a syringe at the site where bone formation is desired. The gel may be a chemical gel which may be a chemical gel formed by primary bonds, and controlled by pH, ionic groups, and/or solvent concentration. The gel may also be a physical gel which may be formed by secondary bonds and controlled by temperature and viscosity. Examples of gels include, but are not limited to, pluronics, gelatin, hyaluronan, collagen, polylactide-polyethylene glycol solutions and conjugates, chitosan, chitosan & b-glycerophosphate (BST-gel), alginates, agarose, hydroxypropyl cellulose, methyl cellulose, polyethylene oxide, polylactides/glycolides in N-methyl-2-pyrrolidone. See for example, Anatomical Record (2001), 263 (4), 342-349, the teachings of which are incorporated herein by reference.

In one embodiment, the formulation can include a polymeric carrier that may be photopolymerizable, such as by electromagnetic radiation with wavelength of at least about 250 nm. Example of photopolymerizable polymers include polyethylene (PEG) acrylate derivatives, PEG methacrylate derivatives, propylene fumarate-co-ethylene glycol, polyvinyl alcohol derivatives, PEG-co-poly(-hydroxy acid) diacrylate macromers, and modified polysaccharides such as hyaluronic acid derivatives and dextran methacrylate. See for example, U.S. Pat. No. 5,410,016, herein incorporated by reference.

In one embodiment, the formulation can include a carrier that is temperature sensitive. Examples include carriers made from N-isopropylacrylamide (NiPAM), or modified NiPAM with lowered lower critical solution temperature (LCST) and enhanced peptide (e.g. NELL1) binding by incorporation of ethyl methacrylate and N-acryloxysuccinimide; or alkyl methacrylates such as butylmethacrylate, hexylmethacrylate and dodecylmethacrylate (PCT Int. Appl. WO/2001070288; U.S. Pat. No. 5,124,151, the teachings of which are incorporated herein by reference).

In one embodiment, the formulation can include a carrier that can have a surface that is decorated and/or immobilized with cell adhesion molecules, adhesion peptides, and adhesion peptide analogs which may promote cell-matrix attachment via receptor mediated mechanisms, and/or molecular moieties which may promote adhesion via non-receptor mediated mechanisms binding such as, but not limited to polycationic polyamino-acid-peptides (e.g. poly-lysine), polyanionic polyamino-acid-peptides, Mefp-class adhesive molecules and other DOPA-rich peptides (e.g. poly-lysine-DOPA), polysaccharides, and proteoglycans. See for example, PCT Int. Appl. WO/2004005421; WO/2003008376; WO/9734016, the teachings of which are incorporated herein by reference.

In one embodiment, the formulation can include a carrier that may include buffering agents such as, but not limited to glycine, glutamic acid hydrochloride, sodium chloride, guanidine, heparin, glutamic acid hydrochloride, acetic acid, succinic acid, polysorbate, dextran sulfate, sucrose, and amino acids. See for example, U.S. Pat. No. 5,385,887, herein incorporated by reference. In one embodiment, the carrier may include a combination of materials such as those listed above.

In some embodiments, the formulation can include a carrier that comprises PLGA/collagen carrier membrane.

In some embodiments, the polymer can be MA or acrylic acid based polymer or prepolymer. For example, the formulation can include a prepolymerized poly-methyl methacrylate (PMMA) and a liquid part of methyl methacrylate (MMA).

In some embodiments, the formulation can include a polymer that is non-MMA or non-acrylic acid polymer. Such a polymer can be biodegradable or non-degradable. In some embodiments, the polymer is poly(lactic acid), poly(lactic-co-glycolic acid) (PLGA), poly(hydroxyalkanoate), or polymers or copolymers of a lactone. In some embodiments, the formulation can include calcium phosphate-based materials.

In some embodiments, the formulation can include a natural material such as cellulose and starch.

In some embodiments, the formulation can explicitly exclude any of the polymers or natural materials mentioned above.

The pharmaceutically acceptable carrier can be any carrier. In some embodiments, the carrier can be saline, an alcohol, culture media or biological liquid buffers.

In some embodiments, the composition can be formulated into any formulation (e.g., a bone substitute material) suitable for use for treating, preventing, or ameliorating any of the above bone conditions, which a person of ordinary skill in the art can readily design and make according to established methods or processes.

In some embodiments, the formulation can explicitly exclude any of the carriers mentioned above.

Method of Use

The composition described herein can be readily formulated by an ordinary artisan into different formulations for treating, preventing or ameliorating a bone, cartilage or vertebra related condition. The composition is effective for wound healing, repair, generation and regeneration of a bone condition. In some embodiments, the composition is effective as a substitute material of a bone condition.

In some embodiments, the bone related conditions includes fractures such as femoral neck fracture, neck bone fracture and wrist fracture, cancer and injury-induced defect, disease-related bone loss, such as bone loss after tooth extraction and periodontal disease-related bone loss, weakened bone quality, arthritis, osteolysis and other degenerative changes or healing of bone tissues, such as in jaw bone, refractory bone wound healing, delayed bone healing, bone healing accompanied with bone resorption or conditions that require the placement of metallic and non-metallic implants to stabilize or fix and reconstruction of bone tissues such as total hip replacement. In some embodiments, the bone condition described herein can be conditions in the jaw and craniofacial areas. The method includes administering the composition to a patient having any of such conditions.

The cartilage related conditions includes cancer and injury-induced defect, weakened cartilage quality, arthritis and perforation, disk-displacement and other degenerative changes of cartilage tissues, and refractory joint wound healing and conditions that require the placement of a metallic or non-metallic implant to stabilize or fix and reconstruct joints.

The vertebral related conditions includes spine fracture/disorder or spinal disk displacement, fracture or degenerative changes of vertebral tissues, bone and other tissue defect, recession and degenerative changes caused by cancer, injury, systemic metabolism, infection or aging, or fixation and reconstructive treatment of vertebral tissues.

In some embodiments, the present invention provides a method of treating, preventing or ameliorating a bone, cartilage or vertebra related condition. The method includes administering the composition to a patient having the bone, cartilage or vertebra related condition. The mode of administration can be implanting, direct injection, coating on metallic or non-metallic artificial implants, or placing around an implant (e.g., a metallic or non-metallic artificial implant).

In some embodiments, the formulation can be used for bone or cartilage repair in a human being. For example, the human being can be a male or female. The human being can be in any age group. In some embodiments, the human being can have an age of about 25 or above.

The embodiments of the present invention will be illustrated by the following set forth example. All parameters and data are not to be construed to unduly limit the scope of the embodiments of the invention.

EXAMPLE 1

Studies on an Osteogenic Enhancing Composition Comprising NAC

Methods
Osteoblastic Cell Culture

Bone marrow cells isolated from the femur of 8-week-old male Sprague-Dawley rats were placed into alpha-modified Eagle's medium supplemented with 15% fetal bovine serum, 50□g/ml ascorbic acid, $10^{-8}$M dexamethasone, 10 mM Na-β-glycerophosphate and Antibiotic-antimycotic solution containing 10,000 units/ml Penicillin G sodium, 10,000 mg/ml Streptomycin sulfate and 25 mg/ml Amphotericin B. Cells were incubated in a humidified atmosphere of 95% air, 5% $CO_2$ at 37° C. At 80% confluency, the cells were detached using 0.25% Trypsin-1 mM EDTA-4Na and seeded either the polystyrene dish with or without NAC addition, bone substitute material (demineralized bone matrix, Orthoblast, IsoTis OrthoBiologics, Inc. Irvine, Calif.), collagen gel (PureCol, Inamed, Fremont, Calif.) or bone cement (Endurance MV, DePuy Orthopaedics, Warsaw, Ind.) with or without NAC incorporation at a density of $4\times10^4$ cells/cm$^2$. The culture medium was renewed every three days. The NAC incorporated bone graft substitute and collagen membrane materials were prepared by soaking each of the materials in NAC for 24 hours. The NAC-incorporated collagen gel was prepared by mixing the collagen gel and NAC.

Gene Expression Analysis

The expression of bone-related genes was analyzed using the reverse transcription-polymerase chain reaction (RT-PCR). Total RNA in the cultures was extracted using TRIzol (Invitrogen, Carlsbad, Calif.) and purification column (RNeasy, Qiagen, Valencia, Calif.). Following DNAse I treatment, reverse transcription of 0.5 µg of total RNA was performed using MMLV reverse transcriptase (Clontech, Carlsbad, Calif.) in the presence of oligo(dT) primer (Clontech, Carlsbad, Calif.). The PCR reaction was performed using Taq DNA polymerase (EX Taq, Takara Bio, Madison, Wis.) to detect alpha-I type I collagen (collagen I), osteopontin, and osteocalcin mRNA. The primer sequences and PCR conditions are described previously. Resulting products were visualized on 1.5% agarose gel with ethidium bromide staining. The intensity of bands was quantified under UV light, and the values were normalized with reference to GAPDH mRNA.

Alkaline Phosphatase (ALP) Activity

The cultured osteoblastic cells were washed with Hank's solution twice, and incubated with 120 mM Tris buffer (pH 8.4) containing 0.9 mM naphthol AS-MX phosphate and 1.8 mM fast red TR for 30 min at 37° C. The stained images were analyzed for ALP positive area defined as [(stained area/total dish area)×100)] (%) using a digitized image analysis system (Image Pro-plus, Media Cybernetics, MD). Three independent cultures were evaluated in each the experimental groups.

Mineralization Assays

To determine the mineralizing capability of the osteoblastic cells on the various conditions of bone cement, Von Kossa and Alizarin Red stain techniques were utilized. The mineralized nodule area defined as [(stained area/total dish area)× 100)] (%) was measured using a digitized image analysis system (Image Pro-plus, Media Cybernetics, MD). Three independent cultures were evaluated in each of the experimental groups.

Statistical Analysis

One-way ANOVA was used to assess the ALP, Alizarin Red and Von Kossa staining among the groups, and when appropriate, Bonferroni multiple comparison testing was used; <0.05 was considered statistically significant.

Results

Enhanced Osteogenic Capacity of Osteoblasts by NAC

Figure 1:
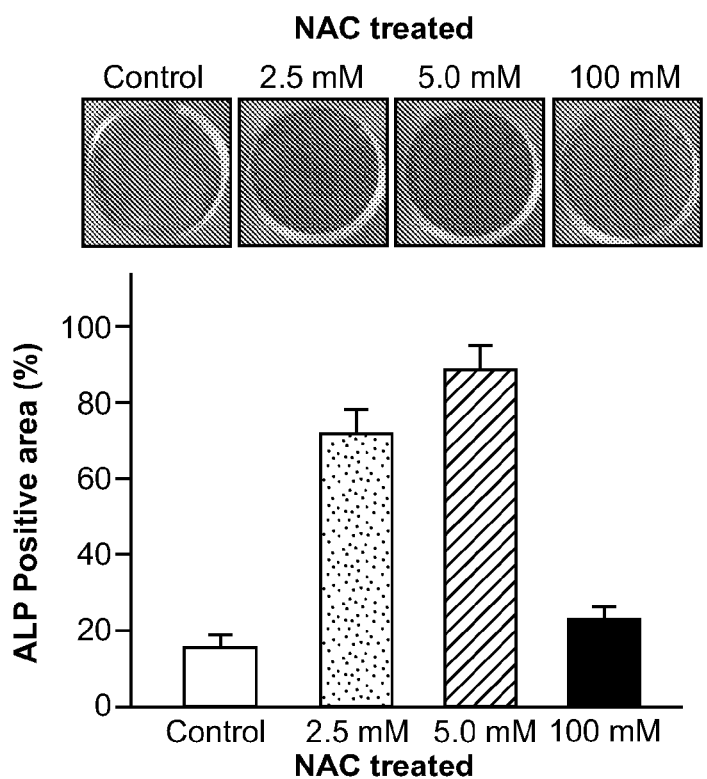
FIG. 1 shows an alkaline phosphatase stain for the osteoblastic culture at day 7 with or without NAC addition in various concentrations. The percentage of the ALP positive area relative to the culture area was measured using a digital image analyzer. Data are shown as the mean±SD (n=3).
Figure 2:
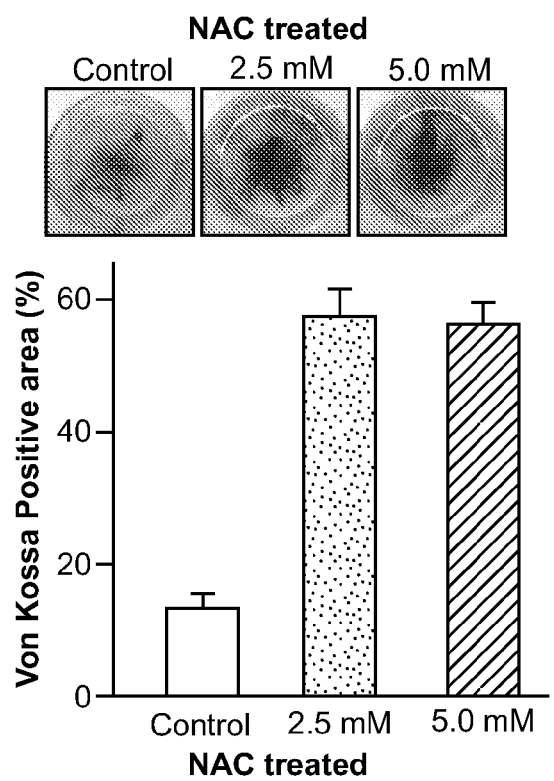
FIG. 2 shows a Von Kossa stain for the osteoblastic culture at day 14 with or without NAC addition into the culture medium. The percentage of the ALP positive area relative to the culture area was measured using a digital image analyzer. Data are shown as the mean±SD (n=3).
Figure 3:
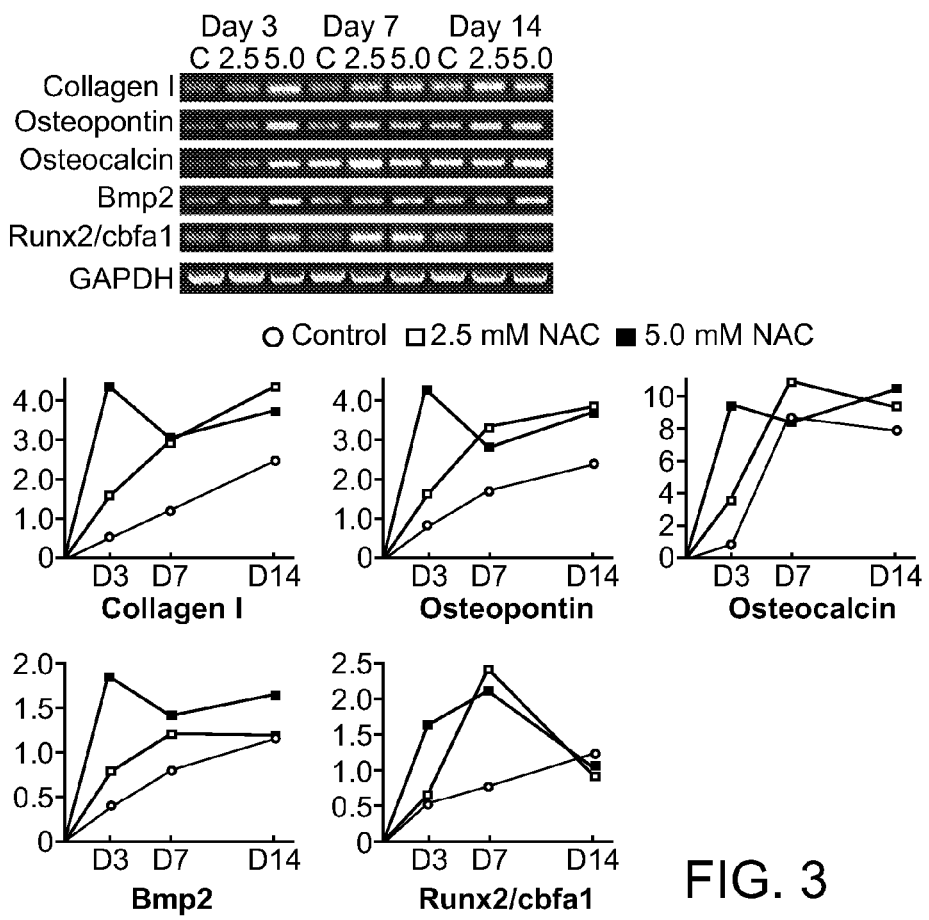
FIG. 3 shows the result of a gene expression analysis for bone-related genes in the osteoblastic culture with or without NAC. A representative image of electrophoresis after RT-PCR (top). Quantitative gene expression levels of collagen I, osteopontin, osteocalcin, bmp2 and runx2/cbfa1 relative to the GAPDH expression (bottom).

The addition of NAC into the osteoblastic culture increased alkaline phosphatase activity at day 7 ($p<0.001$) (FIG. 1). The effect was dose-dependent up to the NAC concentration of 5 mM. Likewise, the NAC addition significantly increased the day 14 Von Kossa positive area in a dose-dependent manner ($p<0.001$), indicating that the NAC addition enhanced the mineralizing capability of osteoblasts ($p<0.001$) (FIG. 2). The expression of collagen I and osteopontin was upregulated in the osteoblastic culture with NAC consistently up top day 14 of culture (FIG. 3). The osteocalcin expression was upregulated in the early stage of day 3 in the culture with NAC, indicating that the osteoblastic differentiation is accelerated by NAC. The gene expression levels of Bmp2 and Runx2/cbfa1 were significantly elevated by NAC addition to the culture, supporting the accelerated differentiation of osteoblasts by NAC.

The results show that adding NAC in the culture accelerates mesenchymal stem cell/osteoblastic differentiation and enhances osteoblastic phenotypes.

Enhanced Osteoconductive Capacity of Various Bone Regenerative and Engineering Materials by NAC A demineralized bone matrix was tested for osteoconductive capacity with or without NAC incorporation. The NAC-incorporated demineralized bone matrix samples showed greater ALP positive area at culture day 14 ($p<0.001$), indicating the NAC-enhanced osteoconductivity.

Figure 4:
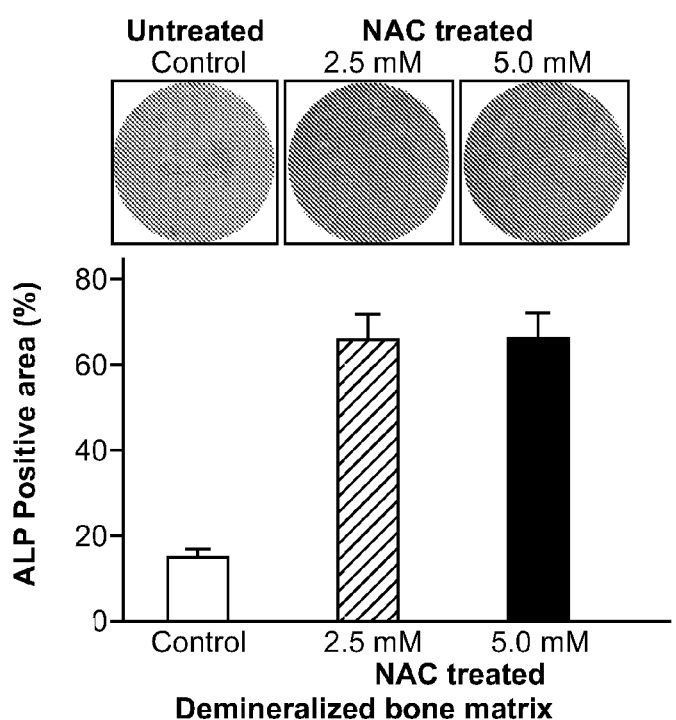
FIG. 4 shows alkaline phosphatase (ALP) activity of the rat osteoblastic cells cultured on demineralized bone matrix materials with or without NAC-incorporation. The top panels show images of ALP staining, and the percentage of the ALP positive area relative to the culture area was measured using a digital image analyzer. Data are shown as the mean±SD (n=3).

FIG. 4 shows alkaline phosphatase (ALP) activity of the rat osteoblastic cells cultured on demineralized bone matrix materials with or without NAC-incorporation. The top panels show images of ALP staining, and the percentage of the ALP positive area relative to the culture area was measured using a digital image analyzer. Data are shown as the mean±SD (n=3).

Figure 5:
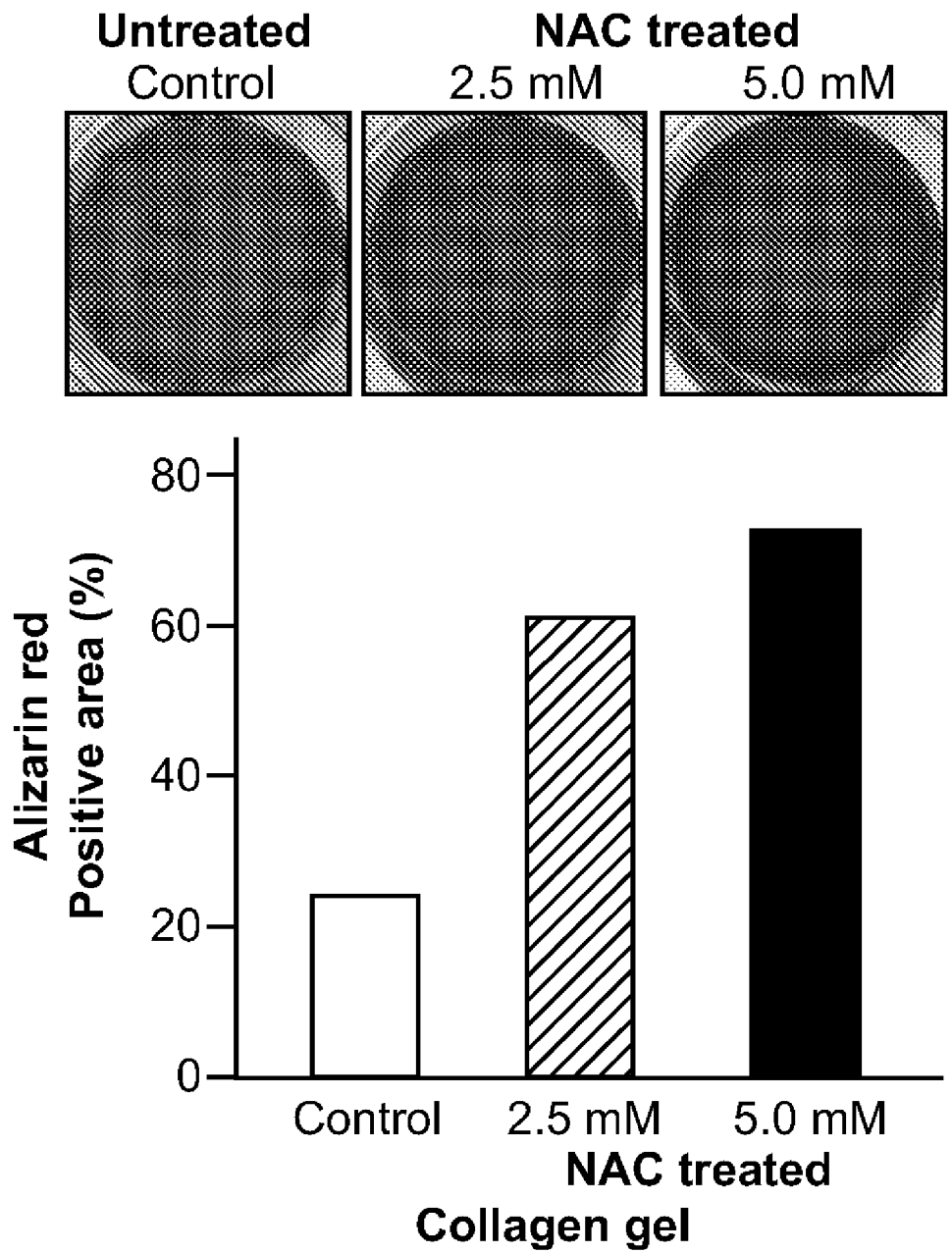
FIG. 5 shows a result of alizarin red stain performed for the rat osteoblastic cells cultured on collagen gel materials with or without NAC addition. The top panels show images of alizarin red staining for calcium, and the percentage of the alizarin red positive area relative to the culture area was measured using a digital image analyzer.
Figure 6:
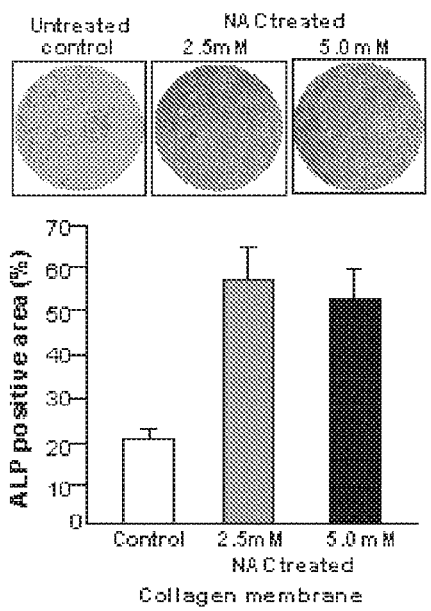
FIG. 6 shows the alkaline phosphatase (ALP) activity of the rat osteoblastic cells cultured on collagen membrane materials with or without NAC-incorporation. The top panels show images of ALP staining, and the percentage of the ALP positive area relative to the culture area was measured using a digital image analyzer. Data are shown as the mean±SD (n=3).
Figure 7A:
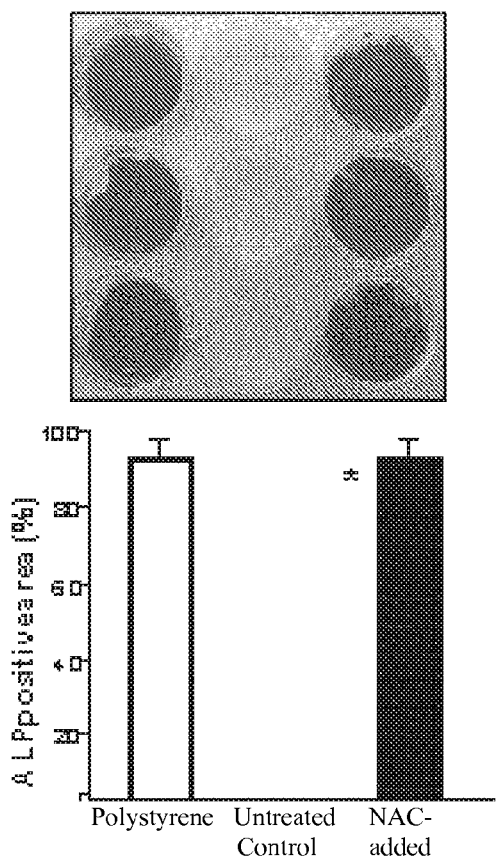
FIGS. 7A and 7B show alkaline phosphatase (ALP) activity (FIG. 7A) and Von Kossa mineralization capacity (FIG.
Figure 7B:
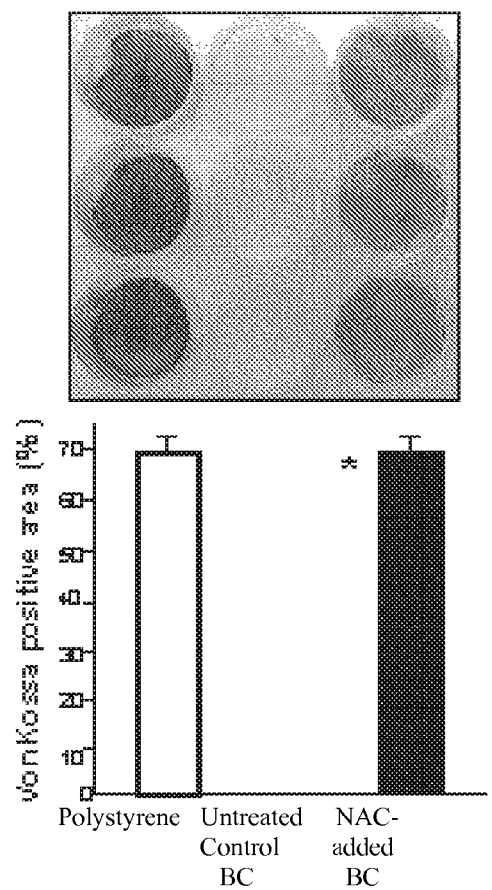

The osteoblasts cultured in the NAC-added collagen gel showed more alizarin red stain compared to the untreated control collagen gel ($p<0.001$), indicating that the collagen gel was more osteoconductive with the addition of NAC (FIG. 5). The osteoblasts cultured on the NAC-incorporated collagen membranes revealed greater ALP positive areas compared to the untreated membrane, showing the enhancement of osteoconductivity of the collagen membrane ($p<0.001$) (FIG. 6). The osteogenic activity was remarkably enhanced on the NAC-added bone cement compared to the untreated control as seen in the ALP activity and Von Kossa mineralization capacity (FIG. 7).

EXAMPLE 2

Studies on a Detoxified and Osteoconductive Cement

Methods

Bone Cement Preparation

Untreated control bone cement was prepared by mixing the recommended ratio of powder and liquid (0.34 g powder and 173.15 µl liquid, Endurance MV, DePuy Orthopaedics, Warsaw, Ind.) for ten seconds in the 12-well culture plate and flattening the surface by a hand instrument and vibration. Experimental bone cement was prepared in two different ways: N-acetyl cysteine (NAC)-treated bone cement and NAC-added bone cement. NAC treated bone cement was prepared in the same manner of the untreated control, but the culture medium contained 5 mM NAC in the medium. The NAC-added bone cement was prepared by mixing 0.34 g powder, 173.15 µl liquid and 5 mM NAC.

Osteoblastic Cell Culture

Bone marrow cells isolated from the femur of 8-week-old male Sprague-Dawley rats were placed into alpha-modified Eagle's medium supplemented with 15% fetal bovine serum, 50 µg/ml ascorbic acid, $10^{-8}$M dexamethasone, 10 mM Na-β-glycerophosphate and Antibiotic-antimycotic solution containing 10,000 units/ml Penicillin G sodium, 10,000 mg/ml Streptomycin sulfate and 25 mg/ml Amphotericin B. Cells were incubated in a humidified atmosphere of 95% air, 5% $CO_2$ at 37° C. At 80% confluency, the cells were detached using 0.25% Trypsin-1 mM EDTA-4Na and seeded onto either the cell culture grade polystyrene dish, bone cement, NAC-treated bone cement (culture on bone cement with NAC in the media), or NAC-added bone cement at a density of $4\times10^4$ cells/cm$^2$. The culture medium was renewed every three days.

Proliferation Assay

Three days and 6 days after seeding, the cells were gently rinsed twice with PBS and treated with 0.1% collagenase in 300 µl of 0.25% trypsin-1 mM EDTA-4Na for 15 min at 37° C. A hematocytometer was used to count the number of detached cells. Selected substrates were examined under scanning electron microscopy to confirm there were no remaining cells. Three independent cultures were prepared for each time points of each of the control bone cement and NAC-added bone cement cultures.

Gene Expression Analysis

The expression of bone-related genes was analyzed using the reverse transcription-polymerase chain reaction (RT-PCR). Total RNA in the cultures was extracted using TRIzol (Invitrogen, Carlsbad, Calif.) and purification column (RNeasy, Qiagen, Valencia, Calif.). Following DNAse I treatment, reverse transcription of 0.5 μg of total RNA was performed using MMLV reverse transcriptase (Clontech, Carlsbad, Calif.) in the presence of oligo(dT) primer (Clontech, Carlsbad, Calif.). The PCR reaction was performed using Taq DNA polymerase (EX Taq, Takara Bio, Madison, Wis.) to detect alpha-I type I collagen (collagen I), osteopontin, and osteocalcin mRNA. The primer sequences and PCR conditions are described previously. Resulting products were visualized on 1.5% agarose gel with ethidium bromide staining. The intensity of bands was quantified under UV light, and the values were normalized with reference to GAPDH mRNA.

Alkaline Phosphatase (ALP) Activity

The day 7 cultured osteoblastic cells were washed with Hank's solution twice, and incubated with 120 mM Tris buffer (pH 8.4) containing 0.9 mM naphthol AS-MX phosphate and 1.8 mM fast red TR for 30 min at 37° C. The stained images were analyzed for ALP positive area defined as [(stained area/total dish area)×100)] (%) using a digitized image analysis system (Image Pro-plus, Media Cybernetics, MD). Three independent cultures were evaluated in each the experimental groups.

Von Kossa Stain

To determine the mineralizing capability of the osteoblastic cells on the various conditions of bone cement, Von Kossa staining was utilized. At day 21 of culture the cells were fixed with 50% ethanol/18% formaldehyde solution for 30 min. The cultures were then incubated with 5% silver nitrate under UV light for 30 min. Finally, the cultures were washed with $ddH_2O$ twice and incubated with 5% sodium thiosulfate solution for 2-5 min. The mineralized nodule area defined as [(stained area/total dish area)×100)] (%) was measured using a digitized image analysis system (Image Pro-plus, Media Cybernetics, MD). Three independent cultures were evaluated in each of the experimental groups.

Detection of Apoptosis

The viability of osteoblastic cells was evaluated by flow cytometric detection of apoptosis (Annexin V-FITC Kit). The method is based on the binding properties of annexin V to phosphatidylserine (PS) and on the DNA-intercalating capabilities of propidium iodide (PI). The osteoblastic cells, incubated on the bone cement or NAC-added bone cement for 24 hours, were tested for cell viability.

Experimental Protocol for Bone Cement Mechanical Testing

Mechanical properties of the untreated control bone cement and NAC-added bone cement were assessed by transverse strength and elastic modulus obtained from 3-point bending and by hardness obtained from micro-Brinell testing, and also by sheer strength between bone cement and titanium obtained by biomechanical push-out test of titanium rods (see, e.g., Ogawa T, et al., *J Dent Res* 79:1857-63 (2000)).

A. Three-Point Bending Test

A three-point bending test (transverse test) was carried out with the rectangular specimen of bone cement at a cross-head speed of 1 mm per minute using a testing machine (Instron Testing Machine Autograph AGF-500D, Shimadzu, Japan) at room temperature. Bone cement was mixed with a manufacture-instructed ratio as described above for 10 seconds, and placed into a preformed stainless steel rectangular mold (2 mm×2 mm×25 mm). After incubating the specimens in 37° C. for 24 hours, the resin specimen was removed from the mold and polished with a #1000 abrasive sand paper. Dimensional measurements of the specimen were performed. The transverse strength (D) and elastic modulus (E) were expressed by the equation $D=3 \times L 1/2 w t^2$ and $E=3 S1/4 \times 3 w t$, respectively, using the distance between the supports (1=20 mm), the maximum load (L) exerted on the specimen, the width (w) and depth (t) of the specimen, and the slope of the initial load-displacement curve (S).

B. Hardness Test

The micro-Brinell hardness test was carried out on the cylinder specimen using micro-Brinell hardness tester (Fuji Shikenki, Tokyo, Japan). Bone cement was mixed for 10 seconds and placed in a preformed stainless steel cylinder mold (10 mm in height, 8.0 mm in diameter). The specimens were allowed to polymerize in 37° C. for 24 hours. Consistent load of 245 N was exerted on the specimen surface for 30 seconds. The value of micro-Brinell hardness (H) was determined by the equation $H=L/(9.8 \pi DT)$, using the load given on the specimen (L=245 N), the diameter of the steel sphere ball used for loading (D=2.5 mm) and the depth of the indentation after 30 seconds (T).

C. Push-Out Test

Push-out test was used to assess the titanium-bone cement interfacial strength (see, e.g., Ogawa T, et al., *J Dent Res* 79:1857-63 (2000)). The cylindrical titanium rods (1 mm in diameter and 2 mm in length) were placed into the acrylic block made of heat-cure hard metheylmethacrylate resin. The acrylic block had pre-made holes of 2 mm in diameter and of 2 mm in height. The bone cement with or without 5 mM NAC was prepared by mixing the powder and liquid as instructed by the manufactures, and the implants pasted with the prepared bone cement were placed into the holes with the implant top surface level and flushed with the resin block top surface. The bone cement was polymerized in a 37° C. for 24 hours. The testing machine (Instron 5544 electromechanical testing system, Instron, Canton, Mass.) equipped with a 2000 N load cell and a pushing rod (diameter=0.8 mm) was used to load the implant vertically downward at a crosshead speed of 1 mm/min. The titanium-bone cement sheer strength was determined by measuring the peak of load-displacement curve.

D. Statistical Analysis.

One-way ANOVA was used to assess the ALP and Von Kossa staining among the groups, and when appropriate, Bonferroni multiple comparison testing was used. The t-test was used to examine mechanical differences between the untreated control bone cement and NAC-added bone cement; <0.05 was considered statistically significant.

Results

Rescue of Osteoblastic Cells by NAC

Flowcytometric analysis revealed that the percentages of viable osteoblastic cells 24 hours after seeding were 76% on the NAC-added bone cement and 56% on the untreated control bone cement, indicating that the addition of NAC prevented the cell death causing from bone cement (FIG. 8). The percentage of apoptotic cells and necrotic cells were reduced by approximately 50% on the NAC-added bone cement compared to the control bone cement.

Restored Osteoblastic Proliferation by NAC

The density of the osteoblastic cells on the NAC-added bone cement was 10-25 times greater than on the control bone cement at both days 3 and 6 of culture (FIG. 9).

Restored Osteogenic Phenotype of Osteoblasts on Bone Cement with NAC

The osteoblasts cultured on the untreated control bone cement for 14 days showed nearly no alkaline phosphatase (ALP) positive staining (FIG. 10A). In contrast, an extensive area of the culture on the NAC-added bone cement, equivalent to the one on the polystyrene culture, was found to be ALP positive. In FIG. 10A, the top panels show images of ALP staining of the osteoblastic cells cultured on either on the polystyrene, untreated control bone cement or NAC-added bone cement. The percentage of the ALP positive area relative to the culture area was measured using a digital image analyzer. Data are shown as the mean±SD (n=3) (*statistically significant between the control and NAC-added bone cement cultures, p<0.0001).

The osteoblastic culture at day 21 on the untreated control bone cement showed nearly no Von Kossa positive mineralized nodule, while the culture on the NAC-added bone cement exhibited the Von Kossa positive area which is comparable to the one on the polystyrene (FIG. 10B). In FIG. 10B, the top panels show the images of Von Kossa staining of the cells cultured on either the polystyrene, control bone cement, the NAC-added bone cement. The percentage of the Von Kossa positive area relative to the culture area was measured using a digital image analyzer. Data are shown as the mean±SD (n=3) (*statistically significant between the control and NAC-added bone cement, p<0.0001). These results indicate that NAC addition to bone cement recovered fully the bone cement-induced complete suppression of osteogenic phenotype to the normal degree.

Restored Osteoblastic Gene Expression on Bone Cement with NAC

The expression of collagen I gene was remarkably down-regulated on the control bone cement (FIG. 11A-11B). Further, the expression of the late stage osteoblastic marker genes, such as osteopontin and osteocalcin, was completely suppressed on the control bone cement. Such suppression of the osteoblastic genes was restored to the same level of the polystyrene culture or even enhanced to the higher degree on the NAC-added bone cement.

Maintained Mechanical Properties of Bone Cement After NAC Addition

Figure 12A:
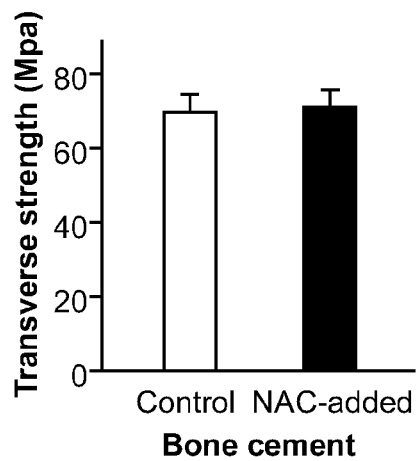
Figure 12B:
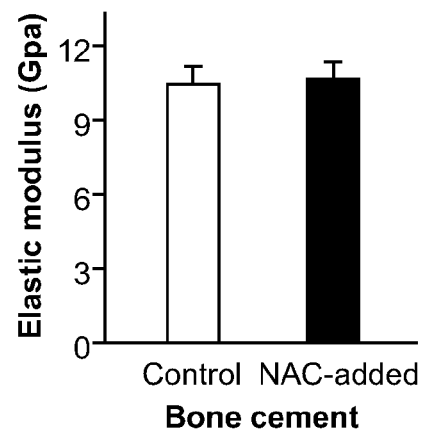
Figure 12C:
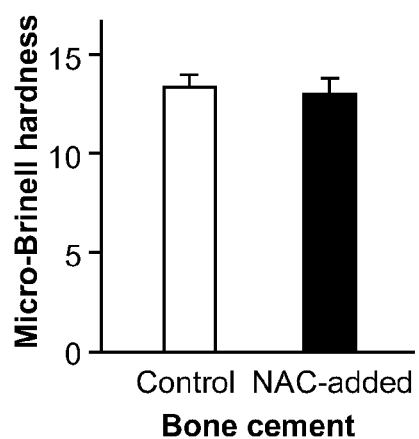
Figure 12D:
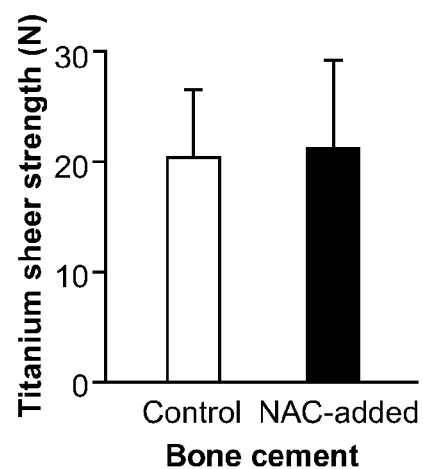

There were no changes in transverse strength, elastic modulus or micro-Brinell surface hardness of bone cement with or without NAC addition (FIGS. 12A-C). Also, NAC addition did not affect the sheer strength between the titanium rod and bone cement (FIG. 12D). FIGS. 12A-D indicate that no significant differences are found between the two types of bone cement in any intrinsic biomechanical parameters tested or titanium-bone cement sheer strength.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A composition comprising N-acetyl cysteine (NAC) in an amount effective for enhancing osteoblastic differentiation and a material selected from the group consisting of a collagen gel, collagen sponge, collage membrane, demineralized bone matrix, bone cement, and a cement or scaffold for bone, cartilage or vertebra, wherein the composition is effective for bone or cartilage repair.

2. The composition of claim 1, further comprising a methacrylate or acrylate based prepolymer.

3. The composition of claim 1, further comprising a biodegradable polymer.

4. The composition of claim 3, wherein the biodegradable polymer is poly(lactic acid), poly(lactic-co-glycolic acid) (PLGA), poly(hydroxyalkanoate), or polymers or copolymers of a lactone.

5. The composition of claim 1, further comprising a non-degradable polymer.

6. The composition of claim 1, further comprising a bioactive agent selected from an adhesion molecule, a bone growth factor, a transforming growth factor (TGF), a transcription factor, fibroblast growth factor (FGF), an insulin like growth factor (IGF), a vascular endothelial growth factor (VEGF), a hormone, an anti-inflammatory agent, calcium phosphate, vitamin, an osteogenic cell, an osteoblastic cell, or combinations thereof 7. The composition of claim 6, wherein the anti-inflammatory agent is selected from steroidal or non-steroidal anti-inflammatory agents, glucocorticoids, or combinations thereof 8. The composition of claim 6, wherein the anti-inflammatory agent is selected from dexamethasone, betamethasone, cortisone, or combinations thereof.

9. The composition of claim 1, further comprising a pharmaceutically acceptable carrier.

10. The composition of claim 1, wherein the material is a cement or scaffold for bone, cartilage or vertebra.

11. The composition of claim 1, wherein the material is collagen gel, collagen sponge, collagen membrane or bone cement.

* * * * *